United States Patent
Cohen et al.

(10) Patent No.: US 10,394,011 B2
(45) Date of Patent: Aug. 27, 2019

(54) PTYCHOGRAPHY SYSTEM

(71) Applicant: TECHNION RESEARCH & DEVELOPMENT FOUNDATION LIMITED, Haifa (IL)

(72) Inventors: Oren Cohen, Haifa (IL); Pavel Sidorenko, Haifa (IL)

(73) Assignee: TECHNION RESEARCH AND DEVELOPMENT FOUNDATION LTD., Haifa (IL)

( * ) Notice: Subject to any disclaimer, the term of this patent is extended or adjusted under 35 U.S.C. 154(b) by 0 days.

(21) Appl. No.: 15/760,832

(22) PCT Filed: Sep. 13, 2016

(86) PCT No.: PCT/IL2016/051019
§ 371 (c)(1),
(2) Date: Mar. 16, 2018

(87) PCT Pub. No.: WO2017/046793
PCT Pub. Date: Mar. 23, 2017

(65) Prior Publication Data
US 2018/0284418 A1 Oct. 4, 2018

Related U.S. Application Data

(60) Provisional application No. 62/219,153, filed on Sep. 16, 2015.

(51) Int. Cl.
*G02B 21/36* (2006.01)
*G01N 23/205* (2018.01)
(Continued)

(52) U.S. Cl.
CPC ......... *G02B 21/365* (2013.01); *G01N 23/205* (2013.01); *G02B 3/0006* (2013.01);
(Continued)

(58) Field of Classification Search
CPC ............... G02B 21/365; G02B 3/0006; G02B 21/0056; G02B 21/06; G02B 21/14;
(Continued)

(56) References Cited

U.S. PATENT DOCUMENTS

| 2014/0118529 A1 | 5/2014 | Zheng et al. |
| 2014/0267674 A1 | 9/2014 | Mertz et al. |
| 2015/0108352 A1 | 4/2015 | Maiden |

FOREIGN PATENT DOCUMENTS

DE 102014101219 8/2015

OTHER PUBLICATIONS

Abbey, et al., Lensless imaging using broadband X-ray sources, Nature Photonics, Jul. 2011, pp. 420-424, vol. 5.
(Continued)

*Primary Examiner* — Wen Huang
(74) *Attorney, Agent, or Firm* — Browdy and Neimark, PLLC

(57) ABSTRACT

A single-exposure ptychography system is presented. The system comprises an optical unit defining an light input plane, an imaging plane, and an object plane between the light input and output planes. The optical unit comprises at least a first focusing assembly, whose front focal plane defines a location of the light input plane; and a diffraction arrangement at a predetermined position with respect to the light input plane. The diffraction arrangement is configured to create from input plane wave light structured light in the form of an array of illuminating beams forming a predetermined illumination pattern in the object plane; thereby providing that each of the illuminating beams creates a different intensity pattern in a known region at the light output plane.

11 Claims, 6 Drawing Sheets

(51) Int. Cl.
  *G02B 21/14* (2006.01)
  *G02B 3/00* (2006.01)
  *G02B 21/00* (2006.01)
  *G02B 21/06* (2006.01)
  *G02B 27/42* (2006.01)
  *G02B 27/46* (2006.01)

(52) U.S. Cl.
  CPC ......... *G02B 21/0056* (2013.01); *G02B 21/06* (2013.01); *G02B 21/14* (2013.01); *G02B 21/367* (2013.01); *G02B 27/4205* (2013.01); *G02B 21/0032* (2013.01); *G02B 27/46* (2013.01)

(58) Field of Classification Search
  CPC .............. G02B 21/367; G02B 27/4205; G02B 21/0032; G02B 27/46; G01N 23/205
  USPC ......................................................... 359/370
  See application file for complete search history.

(56) References Cited

OTHER PUBLICATIONS

Abbey, et al., From Grain Boundaries to Single Defects: A Review of Coherent Methods for Materials Imaging in the X-ray Sciences, JOM, 2013, pp. 1183-1201, vol. 65, No. 9.

Batey, et al., Abstract Only, Information multiplexing in ptychography, Ultramicroscopy, Mar. 2014, pp. 13-21, vol. 138.

Enders, et al., Ptychography with broad-bandwidth radiation, Applied Physics Letters, 2014, pp. 171104-1-171104-5, vol. 104.

Faulkner, et al., Movable Aperture Lensless Transmision Microscopy: A Novel Phase Retrieval Algorithm, Physical Review Letters, Jul. 9, 2004, pp. 023903-1-023903-4, vol. 93, No. 2.

Gazit, et al., Super-resolution and reconstruction of sparse sub-wavelength images, Optics Express, Dec. 21, 2009, pp. 23920-23946, vol. 17, No. 26.

Godden, et al., Ptychographic microscope for three-dimensional imaging, Optics Express, May 19, 2014, pp. 12513-12523, vol. 22, No. 10.

Guizar-Sicairos, et al., Phase retrieval with transverse translation diversity: a nonlinear optimization approach, Optics Express, May 12, 2008, pp. 7264-7278, vol. 16, No. 10.

Guizar-Sicairos, et al., Phase tomography from x-ray coherent diffractive imaging projections, Optics Express, Oct. 24, 2011, pp. 21345-21357, vol. 19, No. 22.

Maiden, et al., An improved ptychographical phase retrieval algorithm for diffractive imaginging, Ultramicroscopy, 2009, pp. 1256-1262, vol. 109.

Maiden, et al., Superresolution imaging via ptychography, Journal of the Optical Society of America, Apr. 2011, pp. 604-612, vol. 28, No. 4.

Ou, et al., Quantitative phase imaging via Fourier ptychographic microscopy, Opt. Lett., Nov. 15, 2013, pp. 4845-4848, 38(22).

Rodenburg, et al., A phase retrieval algorithm for shifting illumination, Applied Physics Letters, Nov. 15, 2004, pp. 4795-4797, vol. 85, No. 2.

Rodenburg, et al., Ptychography and Related Diffractive Imaging Methods, Advances in Imaging and Electron Physics, 2008, pp. 87-184, vol. 150.

Sidorenko, et al., Sparsity-based super-resolved coherent diffraction imaging of one-dimensional objects, Nature Communications, 2015, pp. 1-8.

Tian, et al., 3D intensity and phase imaging from light field measurements in an LED array microscope, Optica, Feb. 2015, pp. 104-111, vol. 2, No. 2.

Zhang, et al., Translation position determination in ptychographic coherent diffraction imaging, Optics Express, Jun. 3, 2013, pp. 13592-13606, vol. 21, No. 11.

Zheng, et al., Wide-field, high-resolution Fourier ptychographic microscopy, Nature Photonics, Sep. 2013, pp. 739-745, vol. 7.

(General Art)

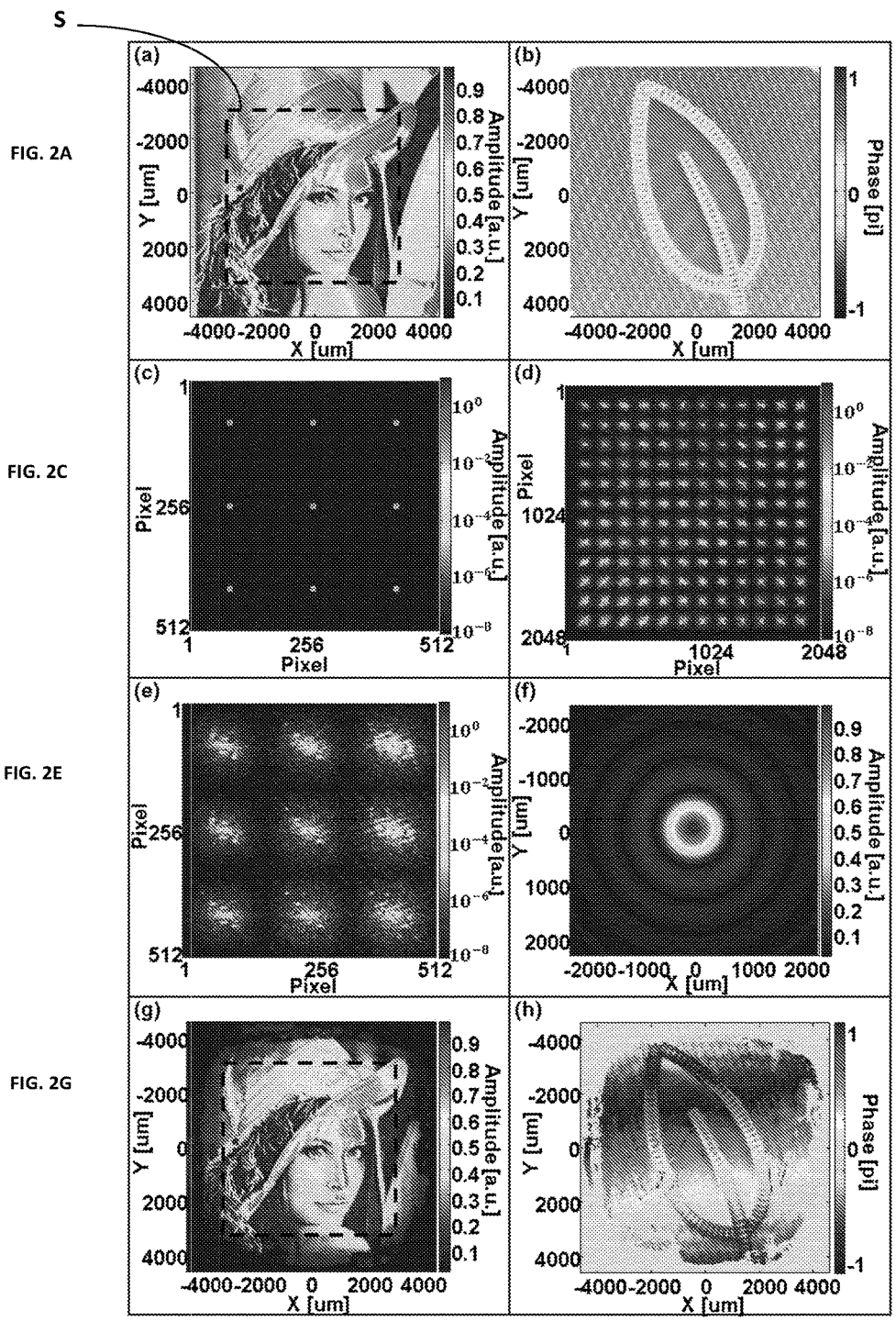

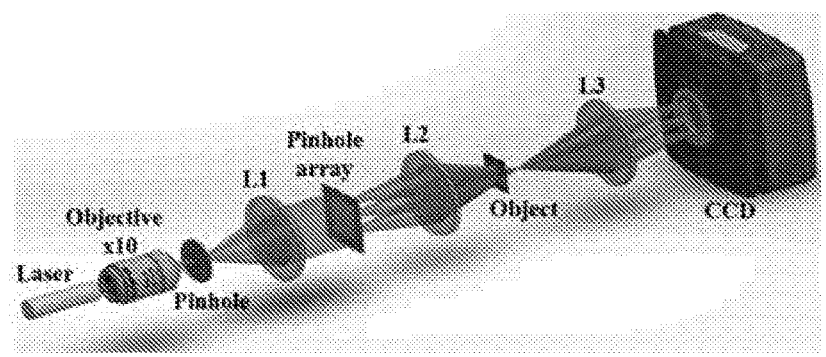
FIG. 3A
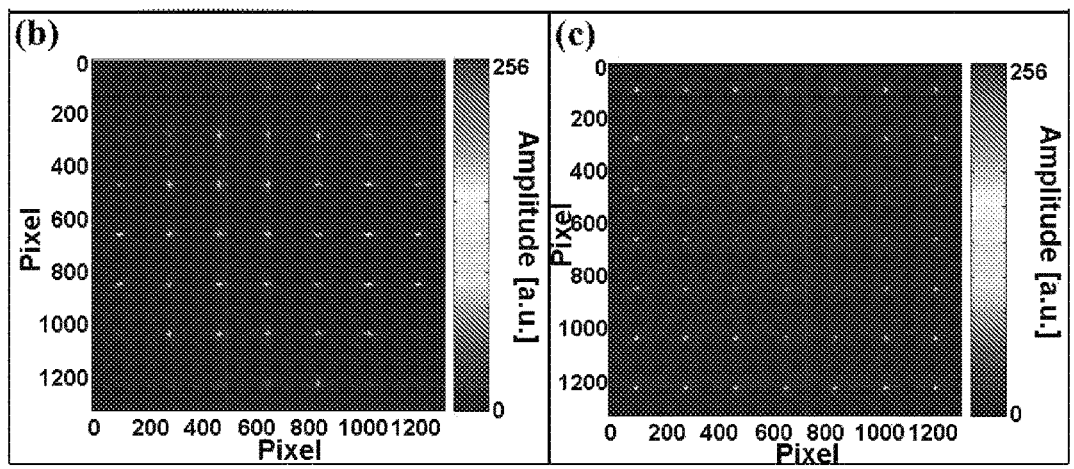
FIG. 3B
FIG. 3C

PTYCHOGRAPHY SYSTEM

This application claims the benefit of priority from U.S. provisional Application No. 62/219,153, filed on Sep. 16, 2015. The content of the above document is incorporated by reference in its entirety as if fully set forth herein.

FIELD OF THE INVENTION

The present invention is generally in the field of imaging techniques, and relates to a ptychography based system.

BACKGROUND OF THE INVENTION

References considered to be relevant as background to the presently disclosed subject matter are listed below:
1. J. M. Rodenburg, "Ptychography and related diffractive imaging methods," in Advances in Imaging and Electron Physics, Vol 150, P. W. Hawkes, ed. (2008), pp. 87-184.
2. B. Abbey, "From Grain Boundaries to Single Defects: A Review of Coherent Methods for Materials Imaging in the X-ray Sciences," Jom 65, 1183-1201 (2013).
3. J. M. Rodenburg and H. M. L. Faulkner, "A phase retrieval algorithm for shifting illumination," Applied Physics Letters 85, 4795-4797 (2004).
4. H. M. L. Faulkner and J. M. Rodenburg, "Movable aperture lensless transmission microscopy: A novel phase retrieval algorithm," Physical Review Letters 93, 023903 (2004).
5. M. Guizar-Sicairos and J. R. Fienup, "Phase retrieval with transverse translation diversity: a nonlinear optimization approach," Optics Express 16, 7264-7278 (2008).
6. A. M. Maiden and J. M. Rodenburg, "An improved ptychographical phase retrieval algorithm for diffractive imaging," Ultramicroscopy 109, 1256-1262 (2009).
7. F. Zhang, I. Peterson, J. Vila-Comamala, A. Diaz, F. Berenguer, R. Bean, B. Chen, A. Menzel, I. K. Robinson, and J. M. Rodenburg, "Translation position determination in ptychographic coherent diffraction imaging," Opt Express 21, 13592-13606 (2013).
8. D. J. Batey, D. Claus, and J. M. Rodenburg, "Information multiplexing in ptychography," Ultramicroscopy 138, 13-21 (2014).
9. A. M. Maiden, M. J. Humphry, F. Zhang, and J. M. Rodenburg, "Superresolution imaging via ptychography," Journal of the Optical Society of America. A, Optics, image science, and vision 28, 604-612 (2011).
10. M. Guizar-Sicairos, A. Diaz, M. Holler, M. S. Lucas, A. Menzel, R. A. Wepf, and O. Bunk, "Phase tomography from x-ray coherent diffractive imaging projections," Optics Express 19, 21345-21357 (2011).
11. B. Abbey, L. W. Whitehead, H. M. Quiney, D. J. Vine, G. A. Cadenazzi, C. A. Henderson, K. A. Nugent, E. Balaur, C. T. Putkunz, A. G. Peele, G. J. Williams, and I. McNulty, "Lensless imaging using broadband X-ray sources," Nature Photonics 5, 420-424 (2011).
12. G. A. Zheng, R. Horstmeyer, and C. H. Yang, "Wide-field, high-resolution Fourier ptychographic microscopy," Nature Photonics 7, 739-745 (2013).
13. X. Z. Ou, R. Horstmeyer, C. H. Yang, and G. A. Zheng, "Quantitative phase imaging via Fourier ptychographic microscopy," Opt. Lett. 38, 4845-4848 (2013).
14. S. Gazit, A. Szameit, Y. C. Eldar, and M. Segev, "Super-resolution and reconstruction of sparse sub-wavelength images," Optics Express 17, 23920-23946 (2009).
15. P. Sidorenko, A. Fleischer, Y. Shechtman, Y. C. Eldar, M. Segev, and O. Cohen, "Sparsity-based super-resolved coherent diffraction imaging of one-dimensional objects," to appear in Nature Communications (2015).
16. B. Enders, M. Dierolf, P. Cloetens, M. Stockmar, F. Pfeiffer, and P. Thibault, "Ptychography with broad-bandwidth radiation," Applied Physics Letters 104, 171104 (2014).
17. T. M. Godden, R. Suman, M. J. Humphry, J. M. Rodenburg, and A. M. Maiden, "Ptychographic microscope for three-dimensional imaging," Optics Express 22, 12513-12523 (2014).
18. L. Tian and L. Waller, "3D intensity and phase imaging from light field measurements in an LED array microscope," Optica 2, 104-111 (2015).

Acknowledgement of the above references herein is not to be inferred as meaning that these are in any way relevant to the patentability of the presently disclosed subject matter.

BACKGROUND

Ptychography is a scanning coherent diffractive imaging (CDI) technique [1, 2] that has recently gained remarkable momentum in optical microscopy in the visible, extreme ultraviolet and x-ray spectral regions, as well as in electron microscopy and other applications, e.g. optical encryption. Ptychography is attractive for bio-imaging and phase imaging because it can provide a label free, high-contrast, quantitative amplitude and phase information.

In ptychography, a complex-valued object is stepped through a localized coherent illumination. In each step, intensity diffraction pattern of the object, typically in a Fraunhofer plan, is measured. The set of typically hundreds diffraction patterns are used for reconstructing a complex image of the object, and simultaneously also the probe beam [3-6].

SUMMARY OF THE INVENTION

The present invention relates, in some embodiments thereof, to single-exposure ptychography system comprising an optical unit defining an light input plane, an imaging plane, and an object plane between the light input and output planes, the optical unit comprising at least a first focusing assembly, a front focal plane of said first focusing assembly defining a location of the light input plane; a diffraction arrangement at a predetermined position with respect to said light input plane, the diffraction arrangement being configured for creating from input plane wave light structured light in the form of an array of illuminating beams forming a predetermined illumination pattern in the object plane; thereby providing that each of the illuminating beams creates a different intensity pattern in a known region at the light output plane.

In a further embodiment, the ptychography system of is configured for performing single-exposure Fourier ptychography.

In a further embodiment, the optical unit is configured such that said predetermined illumination pattern is a spot of superposition of said array of the illuminating beams originated at different locations defined by the diffractive arrangement, the optical unit being configured for imaging said spot into different images having different intensity patterns formed by beams propagated in different directions.

In a further embodiment, the optical unit comprises an 4f optical setup formed by said first focusing unit and a second focusing unit, the object plane being defined by Fourier plane of the 4f setup; and an output MLA for transferring the different Fourier images of the illuminated spots onto different blocks of a pixel matrix in a real image plane.

In a further embodiment, the input plane of the 4f setup is located in a back focal plane of the diffractive arrangement, an output plane of the 4f system is located in a front focal plane of said output MLA, and the output plane of the optical unit is defined by a back focal plane of the output MLA.

In a further embodiment, the diffractive arrangement comprises an input MLA producing an array of localized spots at the input plane of the 4f setup, In further embodiment the present invention relates to a ptychography system configured for performing single-exposure Fourier ptychography, the system comprising an optical unit configured for simultaneously illuminating a region of interest in an object plane by multiple light beams, and forming different images of said region of interest in different regions in an image plane, each of said images having a different intensity pattern formed by beam that propagates at a different angle.

In a further embodiment, the diffractive arrangement comprises an array of apertures, being defined by a pinhole array or a microlens array (MLA).

In a further embodiment, the predetermined illumination pattern is in the form of multiple partially-overlapping spots corresponding to said multiple illuminating beams.

In a further embodiment, the first focusing assembly is configured for focusing the illuminating beams onto a plane spaced-apart from the object plane.

In a further embodiment, the ptychography system comprising an optical unit defining a light input plane, a light output plane for locating a pixel matrix, and an object plane between the light input and output planes, the optical unit comprising: at least a first focusing unit, a front focal plane of said first optical unit defining said input plane; a diffraction arrangement associated with said input plane and configured for creating from input plane wave light a diffracted structured light for illuminating an array of partially-overlapping spots in the object plane.

In a further embodiment, the light output plane is located in a far field of said focusing unit.

In a further embodiment, the diffractive arrangement is located in said input plane.

In a further embodiment, the ptychography system further comprising a light source unit producing said input plane wave light.

In a further embodiment, the light source is configured for producing light of multiple different wavelengths.

In a further embodiment, the light source comprises an array of LEDs producing light of multiple different wavelengths, respectively.

In a further embodiment the ptychography system further comprising a detection unit comprising a pixel matrix and a colored filter.

DESCRIPTION OF THE INVENTION

There is a need in the art for a novel approach in ptychography and Fourier ptychography, enabling single-shot ptychography and single-shot Fourier ptychography.

As described above, ptychography is a particularly powerful coherent diffraction imaging technique. In ptychography, a localized beam is scanned in a step-wise fashion, resulting with array of partially overlapping probing spots on the object. The intensity diffraction pattern from each spot is recorded separately. Then, a complex-valued image is computationally constructed from the set of measured diffraction patterns.

Such property of ptychography as substantial overlapping between the illumination spot in each step with neighboring spots provides significant redundancy in the measured data. This redundancy makes ptychography a very powerful CDI technique that offers several advantages over "conventional" coherent diffraction imaging techniques [1,2]. These strengths include significant improvement in the robustness to noise, no requirement for prior information (e.g. support) on the object and probe beam, no loss of information due to beam stops and generally faster and more reliable reconstruction algorithms.

However, the redundancy is obtained through scanning, resulting with several limitations: First, the temporal resolution is relatively low (the acquisition time is typically in the order of a second or more), precluding the application of ptychography to imaging of fast dynamics. Second, even tiny imprecisions in the scanning steps reduce the resolution of ptychographic microscopes [7]. Third, the space-bandwidth product is limited by the fact that available step motors cannot exhibit both large dynamic range that yields large field of view (FOV) and at the same time very short steps that are crucial for high resolution [7]. Thus, scanning limited resolution, vibration stability, drift and dynamic range weaken the performances of ptychographic microscopes.

The present invention provides a novel ptychographic imaging system (e.g. for microscopes) that benefit from the large redundancy of ptychography and can work in a single-shot, i.e. without scanning, where tens or hundreds of quasi-localized partially-overlapping beams probe the object simultaneously. The invention can be implemented using various schemes for single-shot ptychography and single-shot Fourier ptychography, in both transmission and reflection modes and with coherent and partially coherent illumination. The inventors have experimentally demonstrated single-shot ptychography with 180 millisecond acquisition time, using a sub-milliwatt blue diode laser that simultaneously illuminates the object with 49 partially overlapping beams. Single-shot ptychography, which combines the celebrated power of ptychography with (ultra) fast imaging opens new opportunities in microscopy.

Thus, the invention provides single-shot ptychography: robust ptychograpic microscopes in which tens or hundreds of intensity diffraction patterns from array of partially overlapping illuminating spots are recorded in a single exposure. The invention also provides single-shot Fourier ptychography in which tens or hundreds of beams with partially overlapping illuminating directions are used for obtaining a set of large field-of-view images of the object in a single exposure. Notably the single-shot ptychography (including also single-shot Fourier ptychography) of the invention can be applied across the electromagnetic spectrum, up to the x-ray region. The inventors have analyzed the performances of single-shot ptychograpic microscopy, showing that diffraction limit resolution and large field of view are accessible simultaneously. The combination of the celebrated power of ptychography with the possibility for fast acquisition is advantageous for optical and electronic microscopy, e.g. in bio-imaging.

Thus, according to one broad aspect of the invention, there is provided a ptychography system comprising an optical unit defining an light input plane, an imaging plane, and an object plane between the light input and output planes, the optical unit comprising at least a first focusing assembly, a front focal plane of said first focusing assembly defining a location of the light input plane; a diffraction arrangement at a predetermined position with respect to said light input plane, the diffraction arrangement being configured for creating from input plane wave light structured light in the form of an array of illuminating beams forming a predetermined illumination pattern in the object plane; thereby providing that each of the illuminating beams creates a different intensity pattern in a known region at the light output plane.

The diffracted structured light is created by passing an input plane wave light through an array of apertures, being either a pinhole array or microlens array (MLA).

In some embodiments, the optical unit is configured for simultaneously illuminating an object by (diffracted structured light) formed by the multiple illuminating beams which are partially-overlapping beams in the object plane. To this end, the focusing assembly focuses the illuminating beams onto a plane spaced-apart from the object plane, and focuses diffracted light from the object plane onto a light sensitive surface (pixel matrix) of a detector.

The intensity pattern measured by the pixel matrix can be used for ptychographic reconstruction of the object. Each probe beam (approximately) gives rise to a separate diffraction pattern in the known region (block) in the pixel matrix. Each such block can thus be associated with its diffraction pattern to scattering of a beam that originated from a specific aperture (pinhole/microlens) and illuminated the object at a specific given spot.

Thus, according to another broad aspect of the invention, it provides a ptychography system comprising an optical unit defining a light input plane, a light output plane for locating a pixel matrix, and an object plane between the light input and output planes, the optical unit comprising: at least a first focusing unit, a front focal plane of said first optical unit defining said input plane; and a diffraction arrangement associated with said input plane and configured for creating from input plane wave light a diffracted structured light formed by an array of illuminating beams for illuminating an array of partially-overlapping spots in the object plane, thereby providing that each of the illuminating beams creates a different diffraction pattern in a known region of the pixel matrix.

Preferably, the optical unit also includes an output MLA upstream of the image plane (pixel matrix).

According to yet another aspect of the invention it provides ptychography system and comprising an optical unit configured for simultaneously illuminating an object by multiple beams with partially overlapping propagation directions and an imaging system that forms multiple images (multiple blocks in the pixel matrix), where the detected intensity in each block corresponds (approximately) to radiation that originated from a specific input aperture (pinhole/microlens) and illuminated the object at a specific given propagation direction.

In some embodiments, the optical unit includes an 4f optical setup. The 4f optical setup typically defines an input plane of the optical unit located in a front focal plane of a first lens of the 4f setup and an output (image) plane of the optical unit located at a back focal plane of a second lens of the 4f setup. The pixel matrix is located at the output plane of the optical unit, and a diffractive arrangement is located at the input plane of the optical unit. The diffractive arrangement, which typically includes an array of pinholes or microlenses, is configured for producing the diffracted structure light. The parameters of the 4f setup are selected considering that the object plane is spaced from a Fourier plane of the 4f system a certain non-zero distance ($d \neq 0$). It should be understood that, generally, the optical unit may include only one focusing assembly (with the diffractive arrangement at the front focal plane thereof) for focusing the diffracted structured light onto a plane spaced from the object plane, in which case an image plane (pixel matrix) is located in the far field of the lens assembly.

In preferred embodiments of the invention, the ptychography system is configured for performing single-shot (single-exposure) Fourier ptychography. The optical unit is configured such that an illuminating spot on the object is formed by superposition of multiple illuminating beams originated at different known locations, This spot is imaged into spaced-apart regions in the image plane (blocks in a pixel matrix), such that each of these images presents an image of the object in the form of a different intensity pattern formed by light propagating from the object in a different direction (angle).

More specifically, the optical unit includes an 4f setup, and is configured such that the object plane is located in a Fourier plane of the 4F optical setup, and includes the input diffractive arrangement (preferably MLA) and an output MLA positioned. The elements are arranged such that the input plane of the 4f setup is located in a back focal plane of the input MLA, the output plane of the 4f system is located in a front focal plane of the output MLA, and image plane (output plane of the optical unit) is defined by a back focal plane of the output MLS. An object plane is located in the Fourier plane of the 4f setup ($d=0$). The first input MLA produces array of localized spots at the input plane of the 4f system, and the second output MLA transfers the multiple Fourier images to the output plane of the 4f system where the pixel matrix is located. By this, an array of non-identical images of the object is created on the pixel matrix, where each image is created by a beam that propagates at a different angle. As described above, the detected intensity pattern on the pixel matrix can be divided into blocks, where each block approximately corresponds to an image of the object that was obtained by a beam that propagated at different angle. These blocks form the required set of measurements for Fourier ptychography. It should be understood that the use of the output MLA provides for transforming the image from the Fourier plane to the real space.

Thus, according to yet further embodiment of the invention, there is provided a ptychography system configured for performing single-exposure Fourier ptychography, the system comprising an optical unit configured for simultaneously illuminating a region of interest in an object plane by multiple light beams, and forming different images of said region of interest in different regions in an image plane, each of said images having a different intensity pattern formed by beam that propagates at a different angle.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 2A-2H exemplify numerical demonstration of single-shot ptychography using the system of FIGS. 1B and 1C, where FIGS. 2A and 2B correspond to the amplitude and phase of the original object, showing the region confining the centers of the multiple illuminating probe beams, FIGS. 2C and 2D show measured diffraction pattern without and with the object respectively, FIG. 2E shows zoom in on plot of FIG. 2D showing 9 diffraction patterns, FIG. 2F shows reconstructed probe beam, and FIGS. 2G and 2H show reconstructed amplitude and phase respectively;

FIGS. 3A-3C and 4A-4D illustrate experimental results for the single-shot ptychography, where FIG. 3A illustrates an experimental optical setup, and FIGS. 3B and 3C show measured diffraction patterns with and without the object respectively, FIGS. 4A and 4B show reconstructed amplitude and phase respectively, FIG. 4C shows reconstructed amplitude of the probe beam from measured diffraction patterns, and FIG. 4D shows an image of the object measured by conventional microscope;

FIG. 5A shows the single-shot ptychography using LED array; FIG. 5B shows the single-shot ptychography system configured for operation in reflection mode, and FIG. 5C shows the single-shot ptychography system utilizing a diffraction assembly in the form of micro lens array.

DETAILED DESCRIPTION OF EMBODIMENTS

The invention provides a single-shot (single-exposure) ptychography system and method. In order to better understand the principles of the invention, reference is made to FIGS. 1A, 1B and 1C comparing the conventional (scanning) ptychography (FIG. 1A) and single-shot ptychography (FIGS. 1B and 1C).

Figure 1A:
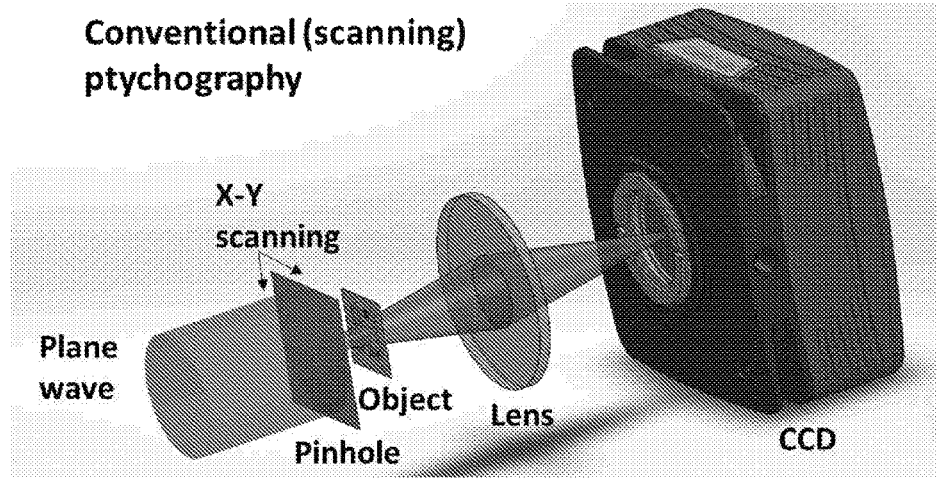
FIG. 1A schematically illustrates an optical setup for conventional (scanning) ptychography.
Figure 1B:
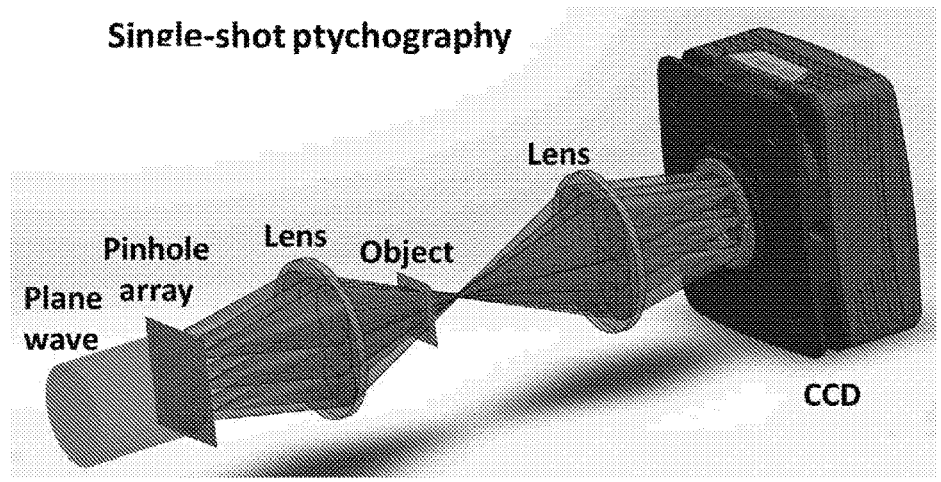
FIG. 1B schematically illustrates a single-shot ptychographical system configured according to some embodiments of the invention using an array of pinholes and plane wave illumination.
Figure 1C:
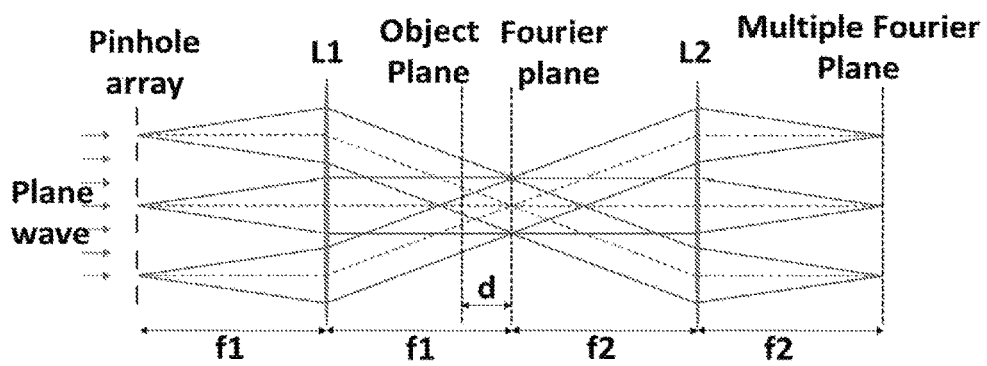
FIG. 1C more specifically illustrates an optical unit and a light propagation scheme in the single-shot ptychographical system of FIG. 1B.

FIG. 1A shows a conventional ptychographical setup with scanning. In a typical scanning ptychographic microscope, a plane wave illuminates a pinhole that is located in front of the object. The charge-coupled device (CCD) image sensor is located in the focal plan of the lens or in the Fraunhofer plan of the object. In both cases, each measured intensity pattern is proportional to the magnitude square of the Fourier transform of the part in the object that was illuminated. After each acquisition, the pinhole is shifted distance R with respect to the object. In this way, multiple diffraction patterns are measured from a set of partially overlapping spots in the object. In ptychography, a single measured intensity pattern corresponds to [1]:

$$I_m(v)=|F[P(r-R_m)O(r)]|^2 \qquad (1).$$

In Eq. (1), $v$ and $r$ are the spatial vectors in the CCD and object planes, respectively, $m=1, 2, 3 \ldots N^2$ is the scanning index and $N^2$ is the total number of steps, F stands for the two-dimensional spatial Fourier operator, O is the complex transmission function of the object, P is the complex envelop of the localized probe beam that illuminates the object and $R_m$ is the center of the illuminated spot in step m.

Efficient algorithms have been developed for reconstructing the object and probe beam from the set of measurements that are described by Eq. (1) [3-6].

Referring to FIGS. 1B and 1C, single-shot ptychography setup with coherent illumination is exemplified. Here, a coherent monochromatic plane wave illuminates a square array of N×N pinholes that is located before or at the input face of an asymmetric 4f system (with lenses L1 and L2 with focal lengths f1 and f2, respectively). Lens L1, with focal distance f1, focuses the light beams that are diffracted from the pinholes onto the object, which is located distance d before the back focal plane of lens L1. Lens L2, with focal distance f2, focuses the diffracted light from the object to the CCD. We assume that the pinholes are circular with diameter D and that the distance between consecutive pinholes is b. The object is located at distance d≠0 before (or after) the Fourier plane of the 4f system, and the CCD is located at the output plan of the 4f system.

It should be noted that the system may utilize a light source unit producing light of multiple wavelengths (e.g. LEDs). The pixel matrix based detector (CCD) may be appropriately equipped with a color filter (Bayer filter).

As shown in FIGS. 1B and 1C, the object is illuminated simultaneously by multiple (m=1, 2, 3 . . . $N^2$) partially-overlapping beams, $\Sigma_m P(r-R_m)\exp(ik_m r)$, where $k_m$ is the transverse k-vector of beam m (every probe beam has a different transversal k-vector). The probe beam complex envelop is quasi-localized (it decays slowly than exponential). For d=0 it is the Airy disk function, $$\frac{D^2 J_1(\pi D r)}{2Dr}$$

(Fourier transform of a circular aperture) where $J_1$ is the first-order Bessel function. For nonzero yet small d, the probe beam still resembles the Airy disk function (an approximate analytic scaling for the width of the probe beam, $$W = \frac{\lambda f_1}{\pi D}\sqrt{1+d\frac{\pi D^2}{\lambda f_1^2}},$$

is obtained by replacing the aperture pinholes array by array of Gaussians with FWHM D).

As can be easily deduced from FIG. 1C, the distance between the centers of adjacent illuminating spots in the object plane (which is the analog to the scanning distance in scanning ptychography) is $R=bd/f_1$. Similarly to the operation of the single lens in scanning ptychography, lens L2 transfers the field after the object to k-space domain at the CCD plan with coordinate transformation $$v = \frac{r}{\lambda f_2}$$

(the fact that the object is located distance $d+f_2$ before lens L2 merely adds a phase, which is not detected by the CCD). Thus, the detected intensity pattern in coherent single-shot ptychography is given by:

$$I(v)=|F[O(r)\Sigma_m P(r-R_m)\exp(ik_m r)]|^2 \qquad (2)$$

The measured intensity pattern in Eq. (2) can be used for ptychographic reconstruction of the object. In other words, each probe beam (approximately) gives rise to a separate diffraction pattern in a known region in the CCD such that Eq. (2) can be approximated by Eq. (1). This is because the effect of $k_m$ is to shift the diffraction pattern laterally in the CCD plane. From straightforward geometry (see FIG. 1C), $|k_m - k_{m-1}| \approx b/f_1$.

Thus, assuming that the power spectra of all the regions in the object (the regions illuminated by the multiple probe beams) are largely confined to a low frequency region with cutoff frequency $\approx b/\lambda f_1$, the intensity pattern of Eq. (2) consists of clearly distinguished $N^2$ diffraction patterns that are located in $N^2$ blocks on the CCD (e.g. see FIG. 2C which will be described more specifically further below). Moreover, each block can be associated with its diffraction pattern to scattering of a beam that originated from a specific pinhole and illuminated the object at a specific given spot. Mathematically, this assumption allows to transfer the sum in Eq. (2) outside the absolute value, then divide the pattern into separate blocks and retrieve a set of intensity patterns in the form of Eq. (1).

Thus, the ordinary reconstruction algorithms of scanning ptychography can be employed to single-shot ptychography. Still, in a sharp contrast to scanning ptychography, here the multiple diffraction patterns from all the beams actually interfere. Thus, when applying ptychographic reconstruction algorithm using the diffraction patterns in the blocks, contributions to a diffraction pattern from beams that originated from other pinholes are regarded as noise.

In order to estimate the resolution of single-shot ptychography, the maximum (i.e. the cutoff) spatial frequency that can be detected under the blocks assumption is calculated. The side of each square block is bM, where $M = f_2/f_1$ is the magnification of the 4f system (the side of the CCD should therefore be larger than $L_{CCD} > NbM$). Thus, taking into account the coordinate transformation $$v = \frac{r}{\lambda f_2},$$

the cutoff frequency is $$v_{max} = \frac{bM}{2\lambda f_2} = \frac{b}{2\lambda f_1}.$$

Importantly, this means that in some spectral regions (e.g. the visible), the resolution in single-shot ptychography can get close to the Abbe resolution limit by using $f_1 \sim b$. Moreover, ptychography was demonstrated to yield a somewhat higher resolution than the measured bandwidth in a single diffraction pattern (which in the present case is $$\frac{1}{2v_{max}}) \,[21].$$

In the limit of very large N, the field of view (with dimension of length) of single-shot ptychography is given by $FOV = NR = Nbd/f_1$. It is also instructive to take the product of $v_{max}$ and FOV (which is proportional to the space bandwidth product [8]):

$$SBP \propto \frac{Nb^2 d}{\lambda f_1^2}.$$

Single-shot ptychography includes many parameters (e.g. N, b, d, $f_1$, $f_2$ and the location of the pinhole array) that can be used for optimization according to specific requirements. For example, using the following parameters that are available in the visible spectral region (by using objective lenses), N=10, b=1.5 mm, d=0.5 mm, $f_1$=1.5 mm and $f_1$=1.5 mm, provides that the cutoff frequency is $$v_{max} = \frac{1}{2\lambda},$$

yielding diffraction limit resolution, and FOV=5 mm. Finally, it is worth noting that combination of the single-shot geometry with scanning is clearly possible and may be used for further optimization.

Reference is made to FIGS. 2A-2F, showing numerical demonstration of an example of single-shot ptychography using the system depicted in FIG. 1C with the following parameters:

$f_1 = f_2 = 75$ mm, d=18.75 mm, b=1.4 mm, D=25 um, N=12, and $\lambda$=405 nm.

Fresnel-Kirchhoff diffraction formula [10] are used for free propagation, while lenses are modeled by phase elements:

$$\exp\left(i\pi \frac{x^2 + y^2}{\lambda f}\right).$$

The amplitude and phase transmissions of the object are displayed in FIGS. 2A and 2B, respectively. The black dashed square S marks the region confining the centers of the 144 illuminating probe beams. The intensity pattern at the exit of the 4f system without the object is calculated and 35 dB white Gaussian noise added. FIG. 2C shows measured diffraction pattern without the object. For visibility, a limited region in the CCD is shown (only 9 diffraction patterns). This measurement is used for locating the centers of the blocks (i.e. the v=0 in each block). Then, the intensity pattern at the exit of the 4f system with the object is calculated and 35 dB white Gaussian noise is added. FIG. 2D shows the measured diffraction pattern with the object, and FIG. 2E shows zoom in on plot of FIG. 2D, showing 9 diffraction patterns. Clearly, $N^2$ diffraction patterns are well distinguished. After dividing the measured intensity pattern into $N^2$ separate diffraction patterns, the extended Ptychographical Iterative Engine (ePIE) reconstruction algorithm [6] was applied, and the probe beam was reconstructed (FIG. 2F; here the scale is different as compared to the other graphs), and the object was also reconstructed (FIGS. 2G and 2H show respectively the reconstructed amplitude and phase). As shown, the reconstruction is good within the illuminating region (the black dashed square S) and degrades outside of it (in ptychography, the phase is reconstructed up to a constant and linear chirp offsets [10]). This numerical example indicates that single-shot ptychography is applicable, even for complex objects.

Reference is made to FIGS. 3A-3C and 4A-4D experimentally demonstrating the principles of the single-shot ptychography.

The experimental setup is shown schematically in FIG. 3A. Laser diode ($\lambda$=405 nm and 1 mW power) is spatially filtered and collimated. The beam illuminates a 7×7 square array of pinholes with b=1.4 mm and D=75 μm that is located at the input face of a symmetric 4f system with f=75 mm. The object is located 18.75 mm before the Fourier plane of the 4f system. The CCD is located at the output face of the 4f system. A sub-milliwatt diode laser ($\lambda$=405 nm and 1 mW power) is spatially filtered and collimated by a 10× objective, a 25 μm pinhole and lens L1 with focal distance 50 mm. The spatially coherent light illuminates an $N^2$=49 (7×7) square array of circular pinholes with b=1.4 mm and D=75 μm that is located at the input plane of a 4f system with $f_1$=$f_2$=75 mm (M=1). The object is placed d=18.75 mm before the Fourier plane of the 4f system.

The intensity patterns were measured with the object (FIG. 3B) and without the object (FIG. 3C). Each diffraction pattern was taken with 180 millisecond exposure time. The 49 diffraction patterns are clearly distinguishable in both plots. The calibration measurement was used (i.e. the one w/o the object) for locating the centers of the blocks and for power normalization of each block in FIG. 3B (because the laser illumination on the pinhole array is not completely uniform). Next, the ePIE reconstruction algorithm was we applied.

Figure 4A:
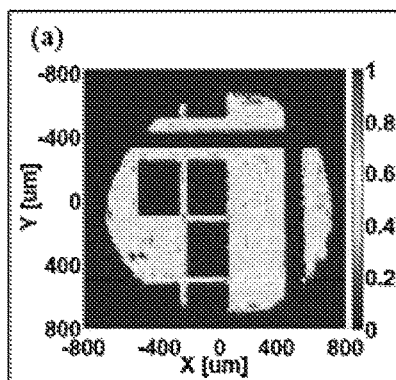
Figure 4B:
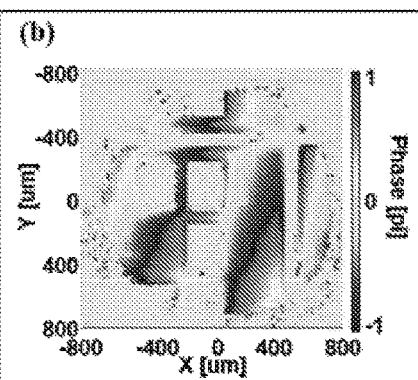
Figure 4C:
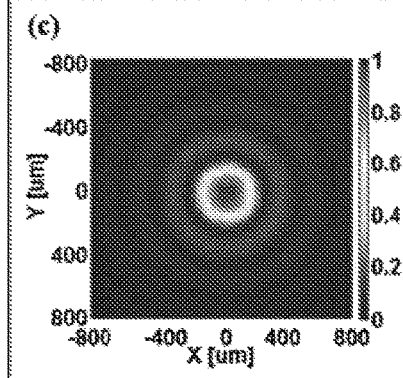
Figure 4D:
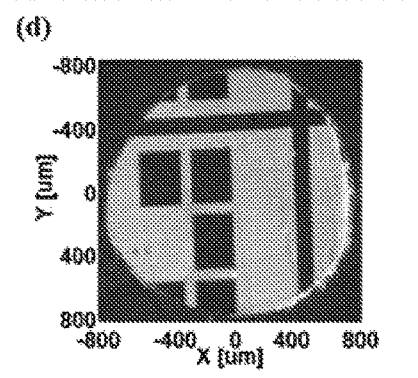

The results are shown in FIGS. 4A-4D. FIGS. 4A and 4B display the reconstructed amplitude and phase of the object, respectively, while FIG. 4C shows the reconstructed probe beam. For comparison, FIG. 4D shows an image of the object using ordinary microscope with ×10 magnification. The agreement between the two images (FIGS. 4A and 4B) is good. The smallest features in this image—two opaque 40 microns squares at the bottom left—are clearly observable in the reconstructed image. These results demonstrate the applicability of single-shot ptychography in real experiments.

The following is the description of some more examples of the schemes for single-shot ptychography.

Referring back to the scheme of FIG. 1B, the pinhole array is illuminated by a coherent wave. It is also possible to illuminate the array by a partially coherent beam with coherence length much larger than the pinhole diameter D and much smaller than the distance b between consecutive pinholes. In this case (partially coherent single-shot ptychography), the detected intensity pattern is given by:

$$I(v)=\Sigma_m |F[O(r)P(r-R_m)\exp(ik_m r)]|^2 \quad (3)$$

By dividing the intensity pattern in Eq. 3 into blocks (in the same form as in coherent single-shot ptychography described above), it can be transferred to a set of intensity patterns that can be used for ptychographic reconstruction. Comparing with coherent single-shot ptychography, the partially coherent case does not contain interferences between beams that originated from different pinholes and may therefore be more robust. Partially-coherent single-shot ptychography is attractive in synchrotrons, because to date, spatial filtering, which results with significant loss of power, is used in CDI experiments [11].

Figure 5A:
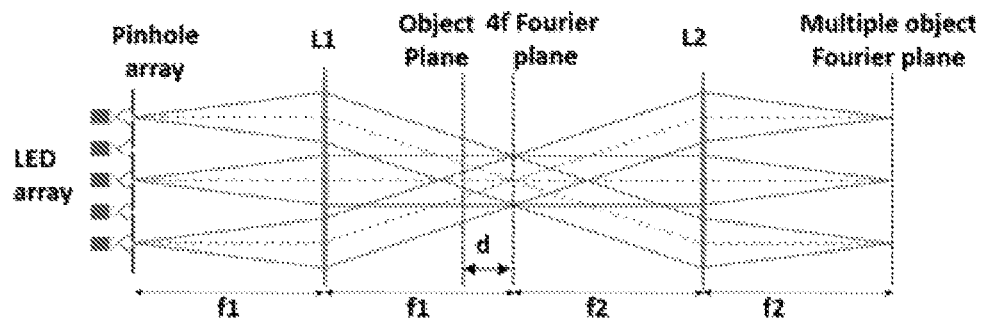
FIGS. 5A-5C show three more examples, respectively, of the optical unit suitable to be used in the single-shot ptychographical system, where
Figure 5B:
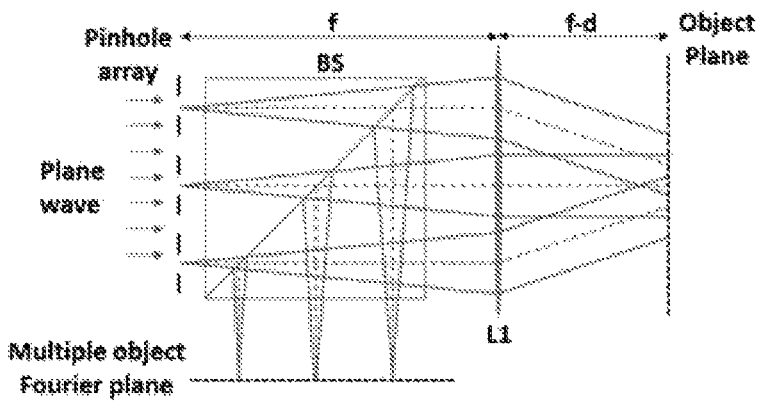
Figure 5C:
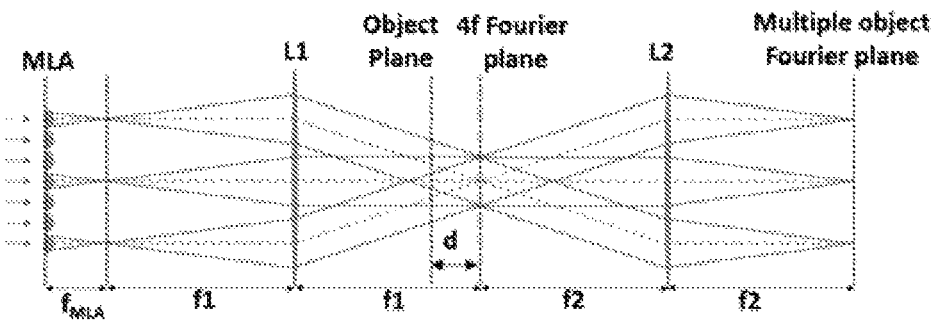
Figure 6:
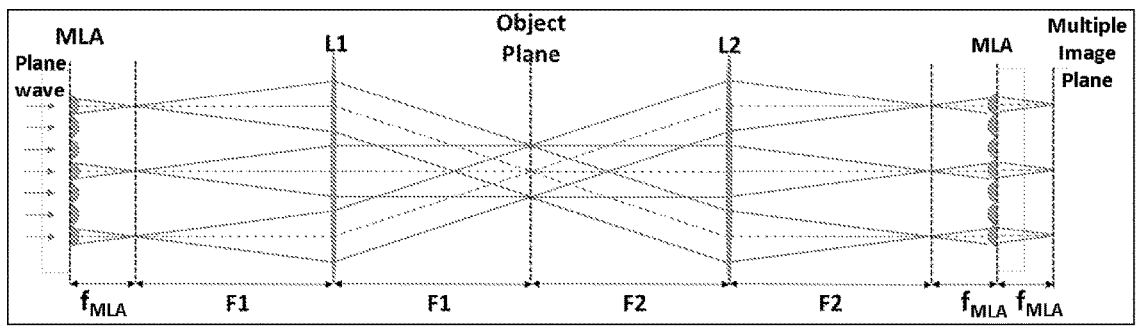
FIG. 6 schematically illustrates an optical unit and light propagation scheme for use in single-shot Fourier ptychography system according to the invention.

Reference is made to FIGS. 5A-5C and 6, exemplifying single-shot "ordinary" ptychography (FIGS. 5A-5C) and FIG. 6 exemplifies single-shot Fourier ptychography.

In the example of FIG. 5A, an array of light emitting diodes (LEDs) is used. Here, the pinhole diameter D is smaller than the coherence length of the radiation from its corresponded LED [12]. Moreover, multicolor LEDs and CCD can be used. For example, using array of Red, Green, and Blue (RGB) LEDs and CCD with corresponding Bayer color filter, a single frame captures three diffraction patterns (of red, green and blue light). Thus, by using multicolor LEDs and CCD, one can, for example, increase the size of each block, by approximately a factor of 3, while maintaining the total number of blocks, and therefore increase the microscope resolution by up to 3 times.

An implementation of single-shot ptychography in reflection mode microscopy is depicted in FIG. 5B. Here, a beam splitter (BS) is placed between the pinhole array and lens L1. Lens L1 converges the beams from the pinhole array to the object and also transfers the field reflected from the object to k-space in the CCD plane.

FIG. 5C displays another, potentially advantageous, modification of single-shot ptychography scheme. Here, a micro lens array (MLA) is used instead of the pinhole array. The MLA is placed before the input plane of the 4f system. In this setup, the MLA collects all the coherent, or partially coherent, illuminated light and forms an array of focal spots at the input of the 4f system. Thus, MLA does not lose optical power. In addition, the focal spots are approximately Gaussians, resulting with more localized probe beams and reduced illumination into neighboring blocks in the CCD.

FIG. 6 shows an example of scheme for single-shot Fourier ptychography. In Fourier ptychography [12, 13], set of low-resolution high-FOV images are recorded, where the probe beam in each measurement propagates at different direction. To date, Fourier ptychography is based on scanning the propagation angle (i.e. the scanning is in Fourier domain). A ptychographic algorithm then reconstructs a high-resolution large-FOV image of the object [12]. The Fourier ptychography setup of the present invention is configured to create multiple different images in the image plane (pixel groups/blocks in the pixel matrix), such that the detected intensity in each image corresponds (approximately) to radiation originated at a specific input aperture (pinhole/microlens) and illuminated the object at a specific given propagation direction.

The setup includes a 4f system and input and output MLAs, with focal distance $f_{MLA}$, located respectively before the input and after the output of the 4f system. The first input MLA (generally, an aperture array) produces array of localized spots at the input face/plane of the 4f system which propagate in different directions (different angular paths) to lens L1 which focuses these different angular light components/beams onto the same spot (region of interest) in an object plane located in the Fourier plane of the 4f system (i.e. d=0). Lens L2 images this spot onto different image spots in output plane of the 4f system, and the second output MLA transfers these multiple Fourier images from the output face of the 4f system to array of non-identical images of the object (region of interest) at the output plane of the optical unit. As shown in the figure, each image is probed by a beam that propagates at a different angle. Similarly to single-shot ptychography, the detected intensity pattern on the CCD (pixel matrix) can be divided into blocks, where each block approximately corresponds to an image of the object that was obtained by a probe beam that propagated at different angle. These blocks form together the required set of measurements for Fourier ptychography.

The inventors have performed numerical and experimental analysis of the single-shot ptychography, and also considered several exemplary schemes for single-shot ptychography and Fourier ptychography. It should be noted that combinations between these schemes is possible, and moreover, can give rise to more possibilities and advantageous. Single-shot ptychographic microscopes utilizing the principles of the invention allow for retrieving the complex (i.e. amplitude and phase) structure of label-free objects within a very short exposure with high (diffraction-limit) resolution and large field of view. Remarkably, single-shot ptychography can be implemented in every spectral region and for every type of waves for which lenses (or other focusing elements) are accessible (in some spectral regions it can be useful to replace the second lens by free propagation). The single-shot ptychographic microscopes can be implemented by modifying commercial confocal microscopes (e.g. adding a pinhole array). It should also be noted that reconstruction algorithms can be further improved to retrieve information that is lost by assumption that the detected intensity pattern consists of non-interacting blocks (i.e. information that is contained in the intensity patterns of Eqs. (2) and (3), but not in Eq. (1)]. Further, structure-based prior knowledge on the object can be used in order to enhance the resolution of single-shot ptychography algorithmically [14,15]. This provides ultrafast sub-wavelength imaging. It should also be noted that although in the examples described above the use of monochromatic radiation is considered, the single-shot ptychography technique of the invention is not limited to these examples. The technique of the invention can be extended to broadband [16] and multi-spectral ptychography [8], that, for example, allows the use of femtosecond laser pulses in single-shot ptychography. The single-shot ptychography can also be combined with recent developments that yielded 3D ptychography [17] and 3D Fourier ptychography [18]. The single-shot ptychography system of the invention may be used with any type of pinhole arrays (lattice structure and shape of pinholes). For example, an array of Gaussians yields localized probe beams and therefore reduces cross-talks between the blocks.

The invention claimed is:

1. A single-exposure ptychography system comprising an optical unit defining a light input plane, a light output plane, and an object plane between the light input and output planes, wherein
the optical unit comprises: at least a first focusing assembly, a front focal plane of the first focusing assembly defining a location of the light input plane;
a light source comprising an array of spaced-apart light emitters producing an array of illuminating beams of partially coherent light and being operable as an array of apertures with an aperture dimension and the space between the apertures being, respectively, smaller and larger than a coherence length of said partially coherent light, said array of the spaced-apart light emitters thereby forming a diffraction arrangement at the light input plane, and creating structured light in the form of an array of illuminating beams creating a predetermined illumination pattern in the object plane, while reducing interferences effects between beams originated from different light emitters in said array of the spaced-apart light emitters; thereby providing that each of the illuminating beams creates a different intensity pattern in a known region in the light output plane.

2. The ptychography system of claim 1, wherein the light emitters are configured for producing said partially coherent light of multiple different wavelengths.

3. The ptychography system of claim 1, wherein said light emitters comprise LEDs.

4. The ptychography system of claim 3, wherein the LEDS produce light of multiple different wavelengths.

5. The ptychography system of claim 1, comprising a detection unit comprising a colored filter and a pixel matrix located in the light output plane.

6. The ptychography system of claim 1, wherein the optical unit is configured such that said predetermined illumination pattern in the light output plane defines an illuminating spot formed by superposition of said array of the illuminating beams originated at the different light emitters defined by the diffractive arrangement, the optical unit being configured for imaging said illumination spot into different images having different intensity patterns formed by beams propagated in different directions.

7. The ptychography system of claim 1, wherein the optical unit comprises:
an 4f optical setup formed by said first focusing assembly and a second focusing unit, the object plane being defined by a Fourier plane of the 4f setup; and
an output microlens array (MLA) for transferring the different images of the illuminated spots from the Fourier plane onto different blocks of a pixel matrix in a real image plane.

8. The ptychography system of claim 1, wherein the diffractive arrangement comprises an array of apertures, being defined by a pinhole array or a microlens array (MLA) at the output of the light emitters.

9. The ptychography system of claim 1, wherein said predetermined illumination pattern is in the form of multiple partially-overlapping spots corresponding to said multiple illuminating beams.

10. The ptychography system of claim 1, wherein said first focusing assembly is configured for focusing the illuminating beams onto a plane spaced-apart from the object plane.

11. The ptychography system of claim 1, wherein the light output plane is located in a far field of said first focusing assembly.

* * * * *